United States Patent [19]

Kreft et al.

[11] Patent Number: 4,732,978
[45] Date of Patent: Mar. 22, 1988

[54] NOVEL SUBSTITUTED NAPHTHYLOXYMETHYL QUINOLINE DERIVATIVES AS ANTI-INFLAMMATORY AND ANTIALLERGY AGENTS

[75] Inventors: Anthony F. Kreft, Trooper; Kenneth L. Kees, West Chester; John H. Musser, Malvern; James J. Bicksler, Eagleville; Winifred P. Howse, Phoenixville, all of Pa.

[73] Assignee: American Home Products Corporation, New York, N.Y.

[21] Appl. No.: 905,619

[22] Filed: Sep. 12, 1986

Related U.S. Application Data

[63] Continuation-in-part of Ser. No. 784,143, Oct. 3, 1985, abandoned.

[51] Int. Cl.$^4$ .................... A61K 31/47; C07D 215/12
[52] U.S. Cl. .................................... 546/152; 544/353; 548/152; 548/217; 548/330; 548/469
[58] Field of Search ...................... 546/152, 153, 178; 514/311, 312, 314

[56] References Cited

U.S. PATENT DOCUMENTS

| | | | | |
|---|---|---|---|---|
| Re. 31,624 | 7/1984 | Dewhirst | ............................ | 546/152 |
| 4,563,526 | 1/1986 | Dewhirst | ............................ | 546/152 |
| 4,631,287 | 12/1986 | Chakraborty | ........................ | 514/307 |
| 4,661,499 | 4/1987 | Young | ................................... | 546/152 |

FOREIGN PATENT DOCUMENTS 181568  5/1986  European Pat. Off. ............ 546/152

*Primary Examiner*—Donald G. Daus
*Assistant Examiner*—Mark W. Noel
*Attorney, Agent, or Firm*—George Tarnowski

[57] ABSTRACT

There are disclosed compounds having the formula

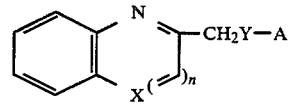

wherein
X is CR or N when n=1; or
X is O, S, NR or CR when n=0;
R is hydrogen or lower alkyl;
Y is —CH$_2$—, —S—, —O— or

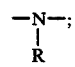

and A is

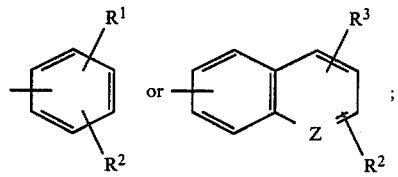

Z is CH or N;
R$^1$ is halo or trifluoromethyl;
R$^2$ is hydrogen or halo;
R$^3$ is hydrogen or halo;
with the proviso that when A is naphthyl, Y is —O— and n=0, X is other than S; and their use in the treatment of inflammatory conditions and in the treatment of leukotriene-medicated naso-bronchial obstructive passageway conditions.

5 Claims, No Drawings

NOVEL SUBSTITUTED NAPHTHYLOXYMETHYL QUINOLINE DERIVATIVES AS ANTI-INFLAMMATORY AND ANTIALLERGY AGENTS

This application is a continuation-in-part of U.S. Ser. No. 784,143 filed Oct. 3, 1985, now abandoned.

This invention relates to novel substituted benzene derivatives possessing lipoxygenase/cyclooxygenase inhibitory activity, which are useful as anti-inflammatory and antiallergy agents.

It is known that arachidonic acid (AA) is metabolized in mammals by two distinct pathways. The metabolism of arachidonic acid by cyclooxygenase enzymes results in the production of prostaglandins and thromboxanes. The physiological activity of the prostaglandins has already been amply elucidated in recent years. It is now known that prostaglandins arise from the endoperoxides $PGG_2$ and $PGH_2$ by the cyclooxygenase pathway of arachidonic acid metabolism. Other products arising from the endoperoxides in the cyclooxygenase pathway are prostacyclin ($PGI_2$) and the thromboxanes $(Tx)A_2$ and $B_2$. In the normal situation, the vasoconstrictive and platelet aggregating properties of the thromboxanes are balanced by prostacyclin ($PGI_2$). There is now considerable evidence that of the various prostaglandin products of cyclooxygenase metabolism of arachidonic acid, $PGE_2$ plays a major role in the development of inflammatory erythema, edema and pain. It is also known now that $PGI_2$ also contributes to these responses. The role of $PGE_2$ in the development of erythema and enhancement of edema explains why cyclooxygenase inhibition agents effectively reduce the redness and swelling associated with most inflammatory conditions [Ferreira and Vane, Handb. Exp. Pharmacol., 50/II, 348–98 (1979)]. $PGE_2$ and $PGI_2$ are also involved in the pain of the inflammatory process; both induce hyperalgesia—sensitization of pain receptors through an edematous reaction or by direct effect—which results in potentiating the pain-producing effects of histamine or bradykinin. The inhibitors of cyclooxygenase, by removing the hyperalgesic cyclooxygenase products, function as analgesics.

In man, cyclooxygenase products have been detected in a number of inflammatory states, including allergic contact eczema, uveitis, arthritis, ulcerative colitis and psoriasis [Higgs et al., in Huskisson, E. C. ed. *Antirheumatic Drugs*, pp. 11–36, Praeger, London. 1983]. Clearly, drugs which exert an effect on the cyclooxygenase pathway of arachidonic acid metabolism are considered to be useful in the treatment of inflammation and inflammatory conditions.

The other pathway of AA metabolism involves lipoxygenase enzymes and results in the production of a number of oxidative products called leukotrienes. The latter are designated by the LT nomenclature system, and the most significant products of the lipoxygenase metabolic pathway are leukotrienes $B_4$, $C_4$, $D_4$ and $E_4$. The substance denominated slow-reacting substance of anaphylaxis (SRS-A) has been shown to consist of a mixture of leukotrienes, $C_4$, $D_4$ and $E_4$ [see Bach et al., *J. Immun.* 215, 115–118 (1980); *Biochem. Biophys. Res. Commun.* 93, 1121–1126 (1980)].

The significance of these leukotrienes is that a great deal of evidence is accumulating showing that leukotrienes participate in inflammatory reactions, exhibit chemotactic activities, stimulate lysosomal enzyme release and act as important factors in the immediate hypersensitivity reaction. It has been shown that $LTC_4$ and $LTD_4$ are potent bronchoconstrictors of the human bronchi [see Dahlen et al., *Nature* 288, 484–486 (1980)], and another leukotriene, $LTB_4$, is a powerful chemotactic factor for leukocytes [see A. W. Ford-Hutchinson, *J. Roy. Soc. Med.*, 74, 831–833 (1981)]. The activity of leukotrienes and slow-reacting substances (SRS's) as mediators of inflammation and hypersensitivity is extensively reviewed in Bailey and Casey, *Ann. Reports Med. Chem.*, 17, 203–217 (1982).

Polymorphonuclear leucocytes (PMN's) are a major source of AA metabolites in the early stages of inflammation and drugs that inhibit leucocyte accumulation in inflamed tissues reduce the concentration of cyclooxygenase products in inflammatory exudates. Thus, cyclooxygenase activity in inflammation may be suppressed through an effect of leucocyte migration. Thus, the suppression of leucocyte migration, which is enhanced by lipoxygenase oxidation products, also contributes to control of the inflammation process.

Accordingly, it is clear that in general inflammatory responses, where PG's are important mediators, dual inhibitors of cyclooxygenase and lipoxygenase must be considered the most useful therapeutic agents. Moreover, the biological activity of leukotrienes and SRS's, and of lipoxygenase as the enzyme leading to the metabolism of AA to leukotrienes, indicates that a rational approach to drug therapy to prevent, remove or ameliorate the symptoms of allergies, anaphylaxis, asthma and inflammation must focus on either blocking the release of mediators of these conditions or to antagonize their effects. Thus compounds, which inhibit the biological effects of the leukotrienes and SRS's and/or which control the biosynthesis of these substances, as by inhibiting lipoxygenase, are considered to be of value in treating such conditions as allergic bronchial asthma, allergic rhinitis, as well as in other immediate hypersensitivity reactions.

It has now been found that certain novel substituted benzene compounds inhibit and/or antagonize products of both the cyclooxygenase and lipoxygenase pathways, and so are useful as anti-inflammatory and antiallergic agents. The present invention provides novel compounds having the following formula:

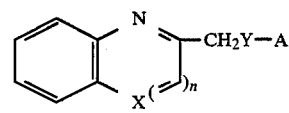

wherein

X is CR or N when n=1; or

X is O, S, NR or CR when n=0;

R is hydrogen or lower alkyl;

Y is —CH$_2$—, —S—, —O— or

A is

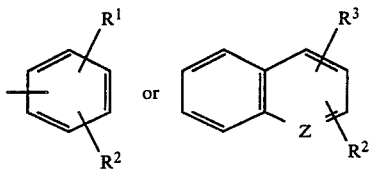

Z is CH or N;
R[1] is halo or trifluoromethyl;
R[2] is hydrogen or halo;
R[3] is hydrogen or halo;
with the proviso that when A is naphthyl, Y is —O— and n=0, X is other than S.

The term "halo" refers to fluoro, chloro and bromo. The term "lower alkyl" refers to moieties having 1 to 6 carbon atoms in the carbon chain.

The compounds of the invention can be prepared in the following manner which is applicable to the preparation of compounds in which Y is O and A is phenyl or naphthyl:

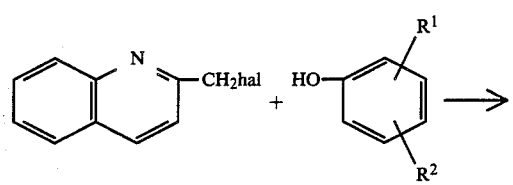

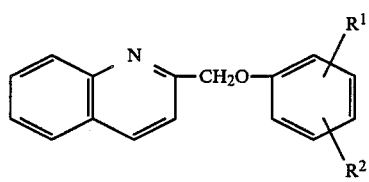

wherein R[1] and R[2] are as defined hereinbefore and hal refers to a halo radical, for example, chloro or bromo. The reaction is carried out in an organic solvent, for example, dimethylformamide, at reduced temperature under a nitrogen atmosphere. The phenyl (or naphthalene) intermediate in the above reaction can be employed in its alkali metal derivative form.

The above reaction can also be carried out by reacting the starting material under reflux in an organic solvent such as for example ethanol, in the presence of a strong base, e.g. an alkali metal hydroxide such as potassium hydroxide.

Compounds in which Y is —S— can be prepared by the following scheme, wherein the reaction is carried out in the presence of triethylamine:

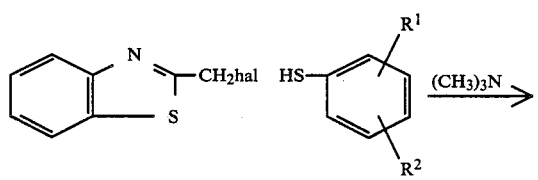

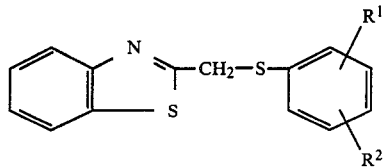

wherein R[1], R[2] and hal are as defined hereinbefore.

The compounds of the invention, by virtue of the ability to inhibit the activity of lipoxygenase enzyme and cyclooxygenase enzyme and to antagonize mediators arising from these enzymatic pathways, are useful in the treatment of inflammatory conditions. Accordingly, the compounds are indicated in the treatment of such disease states as rheumatoid arthritis, osteoarthritis, tendinitis, bursitis and similar conditions involving inflammation. Moreover, by virtue of their ability to inhibit the activity of lipoxygenase enzyme and by their ability to antagonize the effect of $LTC_4$, $LTD_4$ and $LTE_4$ which are the constituents of SRS-A, are useful for the inhibition of symptoms induced by these leukotrienes. Accordingly, the compounds are indicated in the prevention and treatment of those disease states in which $LTC_4$, $LTD_4$ and $LTE_4$ are causative factors, for example allergic rhinitis, allergic bronchial asthma and other leukotriene mediated naso-bronchial obstructive air-passageway conditions, as well as in other immediate hypersensitivity reactions, such as allergic conjunctivitis. The compounds are especially valuable in the prevention and treatment of allergic bronchial asthma.

When the compounds of the invention are employed in the treatment of inflammatory conditions or in the treatment of allergic airways disorders, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The lipoxygenase and cyclooxygenase inhibitory, and leukotriene antagonist and the thromboxane inhibitory effects as well as the antiinflammatory effects of the compounds of the invention may be demonstrated by standard pharmacological procedures, which are described more fully in the examples given hereinafter.

These procedures illustrate the ability of the compounds of the invention to inhibit the polymorphonuclear leukocyte synthesis of the lipoxygenase products 5-HETE; measure the in vivo ability of the compounds to inhibit brochospasm induced by endogenous mediators of bronchoconstriction; measure the ability of the compounds to inhibit the synthesis of $TxB_2$ and $PGE_2$; and measure the in vivo activity of the compounds as lipoxygenase and cyclooxygenase inhibitors in the mouse ear edema assay.

The following examples show the preparation and pharmacological testing of compounds within the invention.

EXAMPLE 1

2-[(3-Bromophenoxy)methyl]quinoline

To 60% sodium hydride (9.8 g, 245 mmol) in 250 mL dimethylformamide at 5° C. under nitrogen is added portionwise 3-bromophenol (42.6 g, 246 mmol). After thirty minutes a solution of 2-(chloromethyl)quinoline (43.6 g, 246 mmol) in 250 mL dimethylformamide is rapidly added. The reaction is allowed to warm to room temperature. After overnight stirring, the reaction is freed of solvent and then partitioned between 1N sodium hydroxide and methylene chloride. The organic layer is separated, dried over magnesium sulfate and evaporated to 67.9 g of a yellow solid. Recrystallization from acetonitrile affords 42.8 g (55%) of brown crystals, m.p. 79°–81° C.

Analysis for: $C_{16}H_{12}BrNO$. Calculated: C, 61.16; H, 3.85; N, 4.46. Found: C, 61.20; H, 3.73; N, 4.56.

EXAMPLE 2

2-[(2-Fluorophenoxy)methyl]quinoline

To a solution of 2-fluorophenol (7.8 g, 70 mmol) in 20 mL ethanol is added 2-(chloromethyl)quinoline hydrochloride (15.0 g, 70 mmol) followed by a solution of potassium hydroxide (7.86 g, 140 mmol) in 50 mL ethanol. The reaction mixture is refluxed overnight. After filtering while still hot, the reaction mixture is cooled to 8° C. to afford 9.3 g (53%) of brown crystals, m.p. 84°–86° C.

Analysis for: $C_{16}H_{12}FNO$. Calculated: C, 75.87; H, 4.78; N, 5.53. Found: C, 75.49; H, 4.71; N, 5.54.

EXAMPLE 3

2-[(3-Chlorophenoxy)methyl]quinoline

The desired compound is prepared using the method of Example 2 but using 3-chlorophenol and modifying the workup as follows: the crude crystals are flushed through Florisil using methylene chloride and recrystallized from hexane to afford 5.1 g (27%) of white crystals, m.p. 71°–73° C.

Analysis for: $C_{16}H_{12}ClNO$. Calculated: C, 71.25; H, 4.48; N, 5.19. Found: C, 71.43; H, 4.46; N, 5.17.

EXAMPLE 4

2-[(4-Chlorophenoxy)methyl]quinoline

The desired compound is prepared using the method of Example 3 but using 4-chlorophenol. White crystals are obtained (8.1 g, 43%), m.p. 92°–94° C.

Analysis for: $C_{16}H_{12}ClNO$. Calculated: C, 71.25; H, 4.48; N, 5.19. Found: C, 71.19; H, 4.45; N, 5.14.

EXAMPLE 5

2-[(3-Fluorophenoxy)methyl]quinoline

The desired compound is prepared using the method of Example 2 but using 3-fluorophenol and modifying the workup as follows: the solvent is removed and the reaction mixture is partitioned between 1N sodium hydroxide and methylene chloride, the organic layer is separated, dried over magnesium sulfate, evaporated to a gum which is chromatographed on silica gel, eluting with 3:1 hexane-ether. The chromatographed material is recrystallized from ethanol to afford 2.0 g (11%) of white crystals. Further recrystallization from hexane affords white crystals, m.p. 68°–70° C.

Analysis for: $C_{16}H_{12}FNO$. Calculated: C, 75.87; H, 4.78; N, 5.53. Found: C, 75.95; H, 4.83; N, 5.46.

EXAMPLE 6

2-[(4-Bromophenoxy)methyl]quinoline

The desired compound is prepared using the method of Example 3 but using 4-bromophenol and doing the final recrystallization from ethanol. White crystals are obtained (8.4 g, 38%), m.p. 103°–105° C.

Analysis for: $C_{16}H_{12}BrNO$. Calculated: C, 61.16; H, 3.85; N, 4.46. Found: C, 60.97; H, 3.77; N, 4.56.

EXAMPLE 7

2-[(3,4-Dichlorophenoxy)methyl]quinoline

The desired compound is prepared using the method of Example 3 but using 3,4-dichlorophenol. White crystals are obtained (10.7 g, 50%), m.p. 80.5°–82.0° C.

Analysis for: $C_{16}H_{11}Cl_2NO$. Calculated: C, 63.18; H, 3.65; N, 4.61. Found: C, 63.18; H, 3.57; N, 4.66.

EXAMPLE 8

2-[(2-Bromophenoxy)methyl]quinoline

The desired compound is prepared using the method of Example 6 but using 2-bromophenol. White crystal are obtained (10.9 g, 50%), m.p. 115°–117° C.

Analysis for: $C_{16}H_{12}BrNO$. Calculated: C, 61.16; H, 3.85; N, 4.46. Found: C, 60.92; H, 3.79; N, 4.40.

EXAMPLE 9

2-[(2-Naphthalenyloxy)methyl]quinoline

The desired compound is prepared using the method of Example 6 but using 2-naphthol. White crystals are obtained (5.3 g, 26%), m.p. 100°–102° C.

Analysis for: $C_{20}H_{15}NO$. Calculated: C, 84.14; H, 5.30; N, 4.91. Found: C 84.15; H, 5.05; N, 4.89.

EXAMPLE 10

2-[(1-Naphthalenyloxy)methyl]quinoline

The desired compound is prepared using the method of Example 5 but using 1-naphthol and changing the elution solvent in 1:1 hexane-methylene chloride and the recrystallization solvent to hexane. White crystals are obtained (6.3 h, 32%), m.p. 99°–101° C.

Analysis for: $C_{20}H_{15}NO$. Calculated: C, 84.14; H, 5.30; N, 4.91. Found: C, 84.07; H, 5.27; N, 4.92.

EXAMPLE 11

2-[(1-Bromo-2-naphthalenyloxy)methyl]quinoline

The desired compound is prepared using the method of Example 6 but using 1-bromo-2-naphthol. White crystals are obtained (7.3 g, 29%), m.p. 130°–132° C.

Analysis for; $C_{20}H_{14}BrNO$. Calculated: C, 65.95; H, 3.87; N, 3.85. Found: C, 65.90; H, 3.85; N, 3.87.

EXAMPLE 12

2-[(6-Bromo-2-naphthalenyloxy)methyl]quinoline

The desired compound is prepared using the method of Example 3 but using 6-bromo-2-naphthol and doing the final recrystallization from toluene. White crystals are obtained (6.9 g, 27%), m.p. 135°–137° C.

Analysis for; $C_{20}H_{14}BrNO$. Calculated: C, 65.95; H, 3.87; N, 3.85. Found: C, 65.84; H, 3.85; N, 3.72.

EXAMPLE 13

2-[(4-Bromophenyl)thio]methyl]benzothiazole

A solution of 2-(chloromethyl)benzothiazole (2.44 g, 13.3 mmol), 4-bromothiophenol (2.26 g, 11.3 mmol) and triethylamine (1.82 g, 18 mmol) is stirred at room temperature overnight. The reaction mixture is poured into 10% hydrochloric acid, and the organic layer is separated and dried over magnesium sulfate. Evaporation of the solvent and recrystallization from hexane affords white crystals, m.p. 65°–67.5° C.

Analysis for: $C_{14}H_{10}BrNS_2$. Calculated: C, 50.01; H, 2.99; N, 4.16. Found: C, 50.06; H, 2.98; N, 4.22.

EXAMPLE 14

2-[(3-Bromophenyl)thio]methyl]benzothiazole

The desired compound is prepared using the method of Example 13 but using 3-bromo thiophenol. Light yellow crystals are obtained, m.p. 61°–64° C.

Analysis for: $C_{14}H_{10}BrNS_2$. Calculated: C, 50.01; H, 2.99; N, 4.16. Found: C, 50.19; H, 3.03; N, 4.17.

EXAMPLE 15

2-[(8-quinolinyloxy)-methyl]quinoline

The title compound is prepared according to the method of Example 1, using 8-hydroxyquinoline. The workup is modified as follows: the solvent is removed and the residue is partitioned between water and chloroform; the organic layer is dried over sodium sulfate and evaporated to an oil which is purified by HPLC and finally recrystallized from isopropyl ether to afford white crystals, m.p. 95°–96° C.

Analysis for: $C_{19}H_{14}N_2O$. Calculated: C, 79.79; H, 4.94; N, 9.80. Found: C, 79.43; H, 4.91; N, 9.73.

EXAMPLE 16

2-[[3-(trifluoromethyl)phenoxy]methyl]quinoline

To a solution of sodium methoxide (1.67 g, 30.84 mmol) in 100 ml of methanol is added 3-trifluoromethylphenol (3.75 ml, 30.84 mmol). After thirty minutes the solvent is removed in vacuo and replaced by 150 ml dimethylformamide. After addtion of 2-(chloromethyl)-quinoline (5.48 g, 30.85 mmol) the reaction mixture is stirred overnight. The solvent is then removed and the residue is partitioned between water and chloroform. The organic layer is dried over sodium sulfate and the solvent is removed. The residue is passed through a silica gel column (eluting with 5:1 hexane-ethyl acetate) and then recrystallized from toluene to afford white crystals (1.4 g, 15%), m.p. 77°–78° C.

Analysis for: $C_{17}H_2F_3NO$. Calculated: C, 67.32; H, 4.00; N, 4.63. Found: C, 67.62; H, 4.06; N, 4.93.

EXAMPLE 17

The compounds 5- and 12-hydroxyeicosatetraenoic acid (5-HETE and 12-HETE) and 5,12-dihydroxyeicosatetraenoic acid (5,12-diHETE) are early arachidonic acid oxidation products in the lipoxygenase cascade, which have been shown to mediate several aspects of the inflammatory and allergic response. The assay of this Example measures the ability of the compounds of the invention to inhibit the synthesis of 5-HETE by rat glycogen-elicited polymorphonuclear leukocytes.

The assay is carried out as follows:

Peritoneal PMN are obtained from female Wistar rats (150–250 g) that received an i.p. injection of 6% glycogen (10 mL). After 24 hours, rats are killed by $CO_2$ asphyxiation and peritoneal cells are harvested by peritoneal lavage using $Ca^{++}$ and $Mg^{++}$ free Hanks' balanced salt solution (HBSS). The peritoneal exudate is centrifuged at 400 g for 10 minutes. After centrifugation, the lavaged fluid is removed and the cell pellet is resuspended in HBSS containing $Ca^{++}$ and $Mg^{++}$ and 10 mM L-cysteine at a concentration of $2 \times 10^7$ cells/mL. To 1 mL portions of cell suspension, test drugs or vehicle are added and incubated at 37° C. for 10 minutes. Following this preincubation, the calcium ionophore (10 μM), A23187, is added together with 0.5 μCi [$^{14}$C] arachidonic acid and further incubated for 10 minutes. The reaction is stopped by the addition of ice cold water (3 mL) and acidifying to pH 3.5. Lipoxygenase products are then extracted twice into diethyl ether. The pooled ether extracts are evaporated to dryness under nitrogen and the residue is redissolved in a small volume of methanol and spotted on aluminum backed pre-coated thin layer chromatographic plates. The samples are then co-chromatographed with authentic reference 5-HETE, in the solvent system—hexane:ether:acetic acid (50:50:3). After chromatography, the areas associated with 5-HETE standard are identified by autoradiography, cut out and quantitated by liquid scintillation.

The compounds of this invention are tested in this assay at a level of 50 μm, unless otherwise noted. The results are summarized in Table 1, where those compounds having an inhibition of >50% are designated by a "+". Some results are express as an $IC_{50}$ value.

TABLE 1

| Compound of Example No. | >50% Inhibitory at 50 μm | $IC_{50}$ μm |
|---|---|---|
| 1 | + | |
| 2 | + | |
| 3 | + | 1.5 |
| 4 | + | |
| 5 | + | 9.9 |
| 6 | + | |
| 7 | + | |
| 8 | + | |
| 9 | + | |
| 10 | + | 0.4 |
| 11 | + | |
| 13 | + | |
| 14 | + | |
| 15 | + | |

TABLE 1-continued

| Compound of Example No. | >50% Inhibitory at 50 μm | IC$_{50}$ μm |
|---|---|---|
| 16 | + | |

The results show that the compounds of this invention have significant activity in inhibiting the synthesis of the arachidonic acid lipoxygenase oxidation product 5-HETE.

EXAMPLE 18

The procedure of Example 17 is also employed for the determination of the ability of the compounds of the invention to inhibit the synthesis of the arachidonic acid cyclooxygenase oxidation products TxB$_2$ and PGE$_2$.

In this assay, the procedure of Example 17 is carried out as described. However, in order to determine cyclooxygenase activity, the samples are cochromatographed with authentic reference TxB$_2$ and PGE$_2$ in the solvent system ethyl acetate:formic acid (80:1) and the upper phase of ethyl acetate:isoctane:acetic acid:water (110:50:20:100). After chromatography, the areas associated with TxB$_2$ and PGE$_2$ standards are identified by autoradiography, cut out and quantitated by liquid scintillation techniques.

The results are calculated as in Example 17.

Testing compounds of this invention in this assay, the following results are obtained.

TABLE 2

| Compound of Example No. | >50% Inhibition at 50 μm | | IC$_{50}$ μm | |
|---|---|---|---|---|
| | TxB$_2$ | PGE$_2$ | TxA$_2$ | PGE$_2$ |
| 1 | + | + | | |
| 2 | + | | | |
| 3 | + | | 7.2 | >100 |
| 4 | + | | | |
| 5 | + | | 3.2 | >100 |
| 6 | + | | | |
| 7 | + | | | |
| 8 | + | + | | |
| 9 | + | + | | |
| 10 | + | + | 6.3 | >100 |
| 11 | + | | | |
| 13 | + | + | | |
| 14 | + | | | |

The results show that compounds of this invention have significant activity in inhibiting the synthesis of the arachidonic acid cyclooxygenase oxidation products TxB$_2$ and PGE$_2$.

EXAMPLE 19

The assay of this Example measures the in vivo ability of the compounds of the invention to inhibit the bronchospasm induced in guinea pigs by endogenous mediators of the bronchoconstriction.

The assay is carried out as follows:

Male Hartley strain guinea pigs weighing 250–350 g are sensitized to chicken ovalbumin (OA) (10 mg i.p.) on days 1 and 3 and used starting on day 26. The animals are anesthetized with pentobarbital sodium (50 mg/kg, i.p.), bilateral vagotomy is performed, and the jugular vein is cannulated for injection of drugs and the carotid artery for monitoring blood pressure. The trachea is cannulated for artificial ventilation by a miniature Starling pump and for indirect measurement of respiratory volume changes as described, infra. Succinylcholine (2 mg/kg, i.v.) is administered to arrest spontaneous respiration. A cyclooxygenase inhibitor, indomethacin (10 mg/kg in tris buffer, i.v. at 9 min.) is administered to shunt arachidonic metabolism to lipoxygenase pathways. One minute later, chlorpheniramine (1.0 mg/kg in saline, i.v.) is given to attenuate the histaminic component of anaphylactic bronchoconstriction. Test drugs (dissolved in propylene glycol, polyethylene glycol or saline) are administered either intraduodenally or by aerosol at 2 or 10 minutes before antigen challenge. Anaphylactic bronchoconstriction is induced by administration by breaths of aerosolized OA (1%) or by intravenous administration of 0.1–0.3 mg/kg OA in saline. Control animals receive solvent (2 mL/kg i.d. or appropriate aerosol) in place of drug.

Respiratory volume changes are determined by a calibrated piston whose travel is recorded, via a linear transducer, on a Beckman Dynograph recorder. Maximal bronchoconstrictor volume is determined by clamping off the trachea at the end of the experiment. Overflow volumes at minutes 1, 3 and 5 are obtained from the recorded charts.

Area under the volume overflow curve (AUC) is estimated, using the overflow values at 1, 3 and 5 minutes, and expressed as a percentage of the maximal overflow AUC (equation 1):

$$\% \max AUC = \frac{3(1 \min) + 4(3 \min) + 2(5 \min)}{10(\max)} \times 100 \quad (1)$$

Drug effects are reported as percent inhibition of % max AUC values obtained from appropriate control animals (equation 2):

$$\% \text{ inhibition} = \frac{\% \max AUC \text{ control} - \% \max AUC \text{ treated}}{\% \max AUC \text{ control}} \times 100 \quad (2)$$

Students t-test for unpaired data is used to determine statistical significance. Dose response curves are generated and ED$_{50}$ doses are interpolated from the regression lines.

Results for a compound of the invention in this assay, using OA for induction of bronchospasm, are given below:

TABLE 3

| Compound administered at 10 minutes before intravenously administered ovalbumin challenge | | |
|---|---|---|
| Compound of Example Number | Dose mg/kg (Intraduodenal) | % Inhibition of MAX AUCI |
| 1 | 50 | >50 |

The results show that the compound tested has significant in vivo activity in inhibiting ovalbumin induced bronchospasm mediated by endogenous products of the lipoxygenase oxidation of arachidonic acid.

EXAMPLE 20

The ability of the compounds of the invention to inhibit the lipoxygenase and/or cyclooxygenase pathways of arachidonic acid is examined in the in vivo arachidonic acid (AA)-/12-O-tetradecanoylphorbol acetate (TPA)-induced murine ear edema test.

According to this test, Swiss Webster female mice (Buckshire), approximately 8 weeks old, are placed into plastic boxes in groups of six. Eight groups of mice receive AA topically on the right ear, and another 8 groups receive TPA topically on the right ear. AA and TPA are dissolved in acetone at concentrations of 100 mg/mL and 100 μg/mL respectively. The phlogistics are applied to the right ear by the means of an automatic pipet. Volumes of 10 μL are applied to the inner and outer surfaces of the ear. Each mouse receives either 2 mg/ear AA or 4 μg/ear TPA. The left ear (control) receives acetone delivered in the same manner. Oral and topical dosing regimens are as follows: (1) drugs are given 30 minutes prior to AA treatment, and (2) drugs are given 30 minutes after treatment with TPA.

Measurements are taken with Oditest calipers, 0-10 mm with 0.01 graduations. The right and left ears are measured after 1 hour AA-induced inflammation and 4 hours after TPA-induced inflammation.

The difference between right and left ear thickness is calculated and the significance is determined by a one way analysis of variance with Dunnett's comparisons to control (P=0.05). Drug effects are expressed as a percent change from control values:

% change from control =

$$\frac{(Rt.\ ear\ -\ Lt.\ ear)drug\ -\ (Rt.\ ear\ -\ Lt.\ ear)control}{(Rt.\ ear\ -\ Lt.\ ear)control} \times 100$$

The results for the compounds of the invention are presented in Table 4. The ED$_{50}$ values are also given for these compounds where this has been determined.

TABLE 4

| Compound of Example No. | Mouse Ear Edema Assay % Change from Control | | | |
|---|---|---|---|---|
| | TOPICAL | | TOPICAL ED$_{50}$ mg/ear | |
| | AA[a] | TPA[b] | AA | TPA |
| 1 | −43* | −62* | 2.0 | 0.7 |
| 2 | −40* | −42 | | |
| 3 | −67* | −60* | 0.3 | ND |
| 4 | −43* | −45* | 1.3 | ND |
| 5 | −63* | −47* | 0.3 | 1.6 |
| 6 | −36* | −22 | | |
| 7 | −54* | −21 | | |
| 8 | −32* | −14 | | |
| 10 | | | 0.3 | 0.7 |
| 15 | 52 | 53 | | |
| 16 | 35 | 22 | | |

[a] = AA 1 mg/ear
[b] = TPA 10 μg/ear
ND = not determined
* = <0.05

The results show that the compounds of the invention demonstrate significant topical activity aginst AA- and TPA-induced mouse ear edema, evidencing an inhibitory effect to acute skin inflammation mediated by products of the lipoxygenase and/or cyclooxygenase pathway.

What is claimed is:

1. A compound having the formula

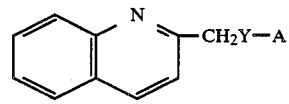

wherein
R is hydrogen or lower alkyl;
Y is —CH$_2$—, —S—, —O— or

and
A is

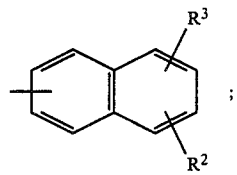

R$^2$ is hydrogen or halo; and
R$^3$ is hydrogen or halo.

2. The compound of claim 1, having the name 2-[(2-naphthalenyloxy)methyl]quinoline.

3. The compound of claim 1, having the name 2-[(1-naphthalenyloxy)methyl]quinoline.

4. The compound of claim 1, having the name 2-[(1-bromo-2-naphthalenyloxy]methyl]quinoline.

5. The compound of claim 1, having the name 2-[(6-bromo-2-naphthalenyloxy)methyl]quinoline.

* * * * *